(12) United States Patent  (10) Patent No.: US 7,899,536 B1
Hellman  (45) Date of Patent: Mar. 1, 2011

(54) MORPHOLOGY DISCRIMINATION FOR CAPTURE ASSESSMENT

(75) Inventor: Heidi Hellman, Studio City, CA (US)

(73) Assignee: Pacesetter, Inc., Sylmar, CA (US)

( * ) Notice: Subject to any disclaimer, the term of this patent is extended or adjusted under 35 U.S.C. 154(b) by 338 days.

(21) Appl. No.: 11/748,925

(22) Filed: May 15, 2007

(51) Int. Cl.
*A61N 1/36* (2006.01)

(52) U.S. Cl. .............................. 607/27; 607/28; 600/509

(58) Field of Classification Search ................ 607/2–6, 607/9, 11, 14–48, 112–130; 600/518, 509
See application file for complete search history.

(56) References Cited

U.S. PATENT DOCUMENTS

| | | | |
|---|---|---|---|
| 4,712,555 A | 12/1987 | Thornander et al. | |
| 4,788,980 A | 12/1988 | Mann et al. | |
| 4,940,052 A | 7/1990 | Mann et al. | |
| 4,944,298 A | 7/1990 | Sholder | |
| 5,350,410 A | 9/1994 | Kleks et al. | |
| 5,417,718 A | 5/1995 | Kecks et al. | |
| 5,466,254 A | 11/1995 | Helland | |
| 5,476,483 A | 12/1995 | Bornzin et al. | |
| 5,779,645 A | 7/1998 | Olson et al. | |
| 5,843,137 A | 12/1998 | Condie et al. | |
| 5,855,594 A * | 1/1999 | Olive et al. | 607/28 |
| 5,902,325 A | 5/1999 | Condie et al. | |
| 6,101,416 A * | 8/2000 | Sloman | 607/28 |
| 6,314,323 B1 | 11/2001 | Ekwall | |
| 6,324,427 B1 | 11/2001 | Florio | |
| 6,501,989 B1 * | 12/2002 | Uhrenius et al. | 607/28 |
| 2003/0050671 A1 | 3/2003 | Bradley | |
| 2003/0083710 A1 | 5/2003 | Ternes et al. | |
| 2003/0083711 A1 | 5/2003 | Yonce et al. | |
| 2005/0137638 A1 * | 6/2005 | Yonce et al. | 607/28 |
| 2007/0021679 A1 * | 1/2007 | Narayan et al. | 600/518 |

FOREIGN PATENT DOCUMENTS

| | | |
|---|---|---|
| EP | 1291038 | 3/2003 |
| WO | WO94/12237 | 6/1994 |
| WO | WO2004026398 | 4/2004 |

* cited by examiner

*Primary Examiner*—Carl H Layno
*Assistant Examiner*—Paula J Stice

(57) ABSTRACT

An exemplary method includes delivering a pacing pulse to a heart, acquiring a cardiac electrogram, comparing the cardiac electrogram to a template and, based on the comparing, deciding if the pacing pulse caused an evoked response. In such a method, the comparing may compare morphology of the cardiac electrogram to the template. Other exemplary methods, devices, systems, etc., are also disclosed.

11 Claims, 7 Drawing Sheets

MORPHOLOGY DISCRIMINATION FOR CAPTURE ASSESSMENT

CROSS-REFERENCE TO RELATED APPLICATIONS

This application is related to copending U.S. patent application Ser. No. 10/405,212, filed Mar. 31, 2003, titled "Diagnosis of Fusion or Pseudofusion," which is incorporated by reference herein.

TECHNICAL FIELD

Subject matter presented herein generally relates to cardiac pacing therapy and, in particular, to use of morphology for capture assessment.

BACKGROUND

Most implantable cardiac pacing devices rely on a power source having a limited amount of energy. To conserve energy, and enhance device longevity, such devices often use an energy level that is just sufficient to pace the heart. However, this energy level may vary over time due to a variety of factors. Consequently, various algorithms have been developed to adjust the energy level, periodically or as needed. As described herein, such algorithms are referred to as threshold search algorithms as they typically search for or uncover an energy level that approximate the threshold energy level required to pace the heart.

When an implantable cardiac pacing device delivers energy to the heart and, in response, the heart contracts in a manner akin to a natural contraction, the delivered energy or pacing pulse is said to have captured. Of course, the delivery of energy is typically timed to correspond to a non-refractory period and to avoid inducing arrhythmia. If the heart does not contract, for any of a variety of reasons, then the delivered energy or pacing pulse is said to have not captured. Threshold search algorithms rely on an ability to distinguish capture and non-capture. At a minimum, they must be able to decide whether capture occurred or to decide whether non-capture occurred. Various threshold search algorithms may include features to decide, independently, whether capture or non-capture occurred.

As described herein, various exemplary methods, devices, systems, etc., use morphology to distinguish capture and non-capture. Such exemplary technologies may infer non-capture when capture is not verified (e.g., morphology fails to verify capture) or infer capture when non-capture is not verified (e.g., morphology fails to verify non-capture). Various exemplary technologies optionally include features to verify capture and to verify non-capture.

SUMMARY

An exemplary method includes delivering a pacing pulse to a heart, acquiring a cardiac electrogram, comparing the cardiac electrogram to a template and, based on the comparing, deciding if the pacing pulse caused an evoked response. In such a method, the comparing may compare morphology of the cardiac electrogram to the template. Other exemplary methods, devices, systems, etc., are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Exemplary Stimulation Device

The techniques described below are intended to be implemented in connection with any stimulation device that is configured or configurable to stimulate nerves and/or stimulate and/or shock a patient's heart.

Figure 1:
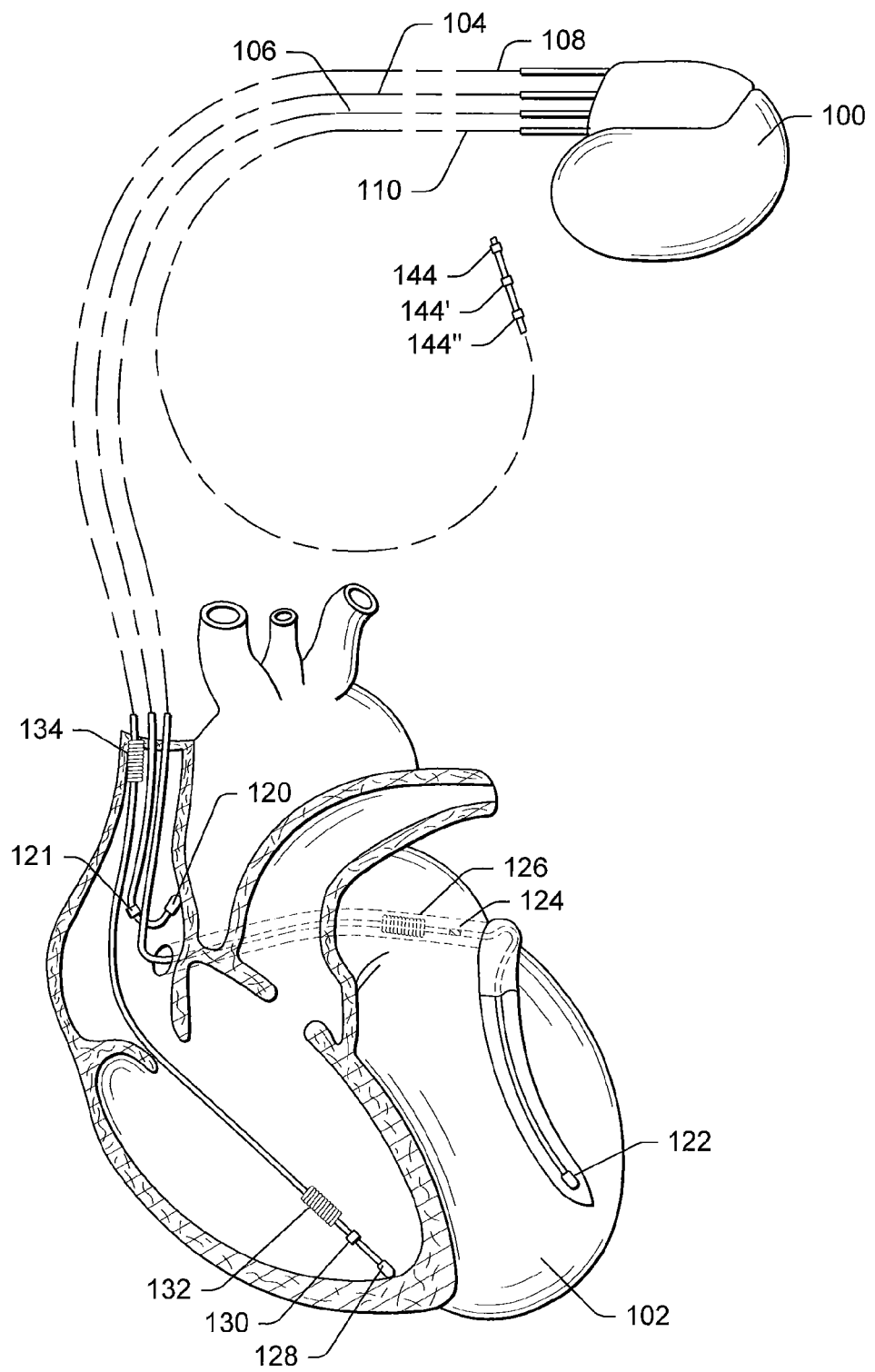
FIG. 1 is a simplified diagram illustrating an exemplary implantable stimulation device in electrical communication with at least three leads implanted into a patient's heart and at least one other lead for sensing and/or delivering stimulation and/or shock therapy. Such a device may include fewer or more leads.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of autonomic nerves and/or detection of other physiologic signals that may be used by the implanted system to modify the pacing parameters. This lead may be positioned in and/or near a patient's heart or near an autonomic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve; such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve; such an electrode may be positioned on the lead or a bifurcation or leg of the lead.

Figure 2:
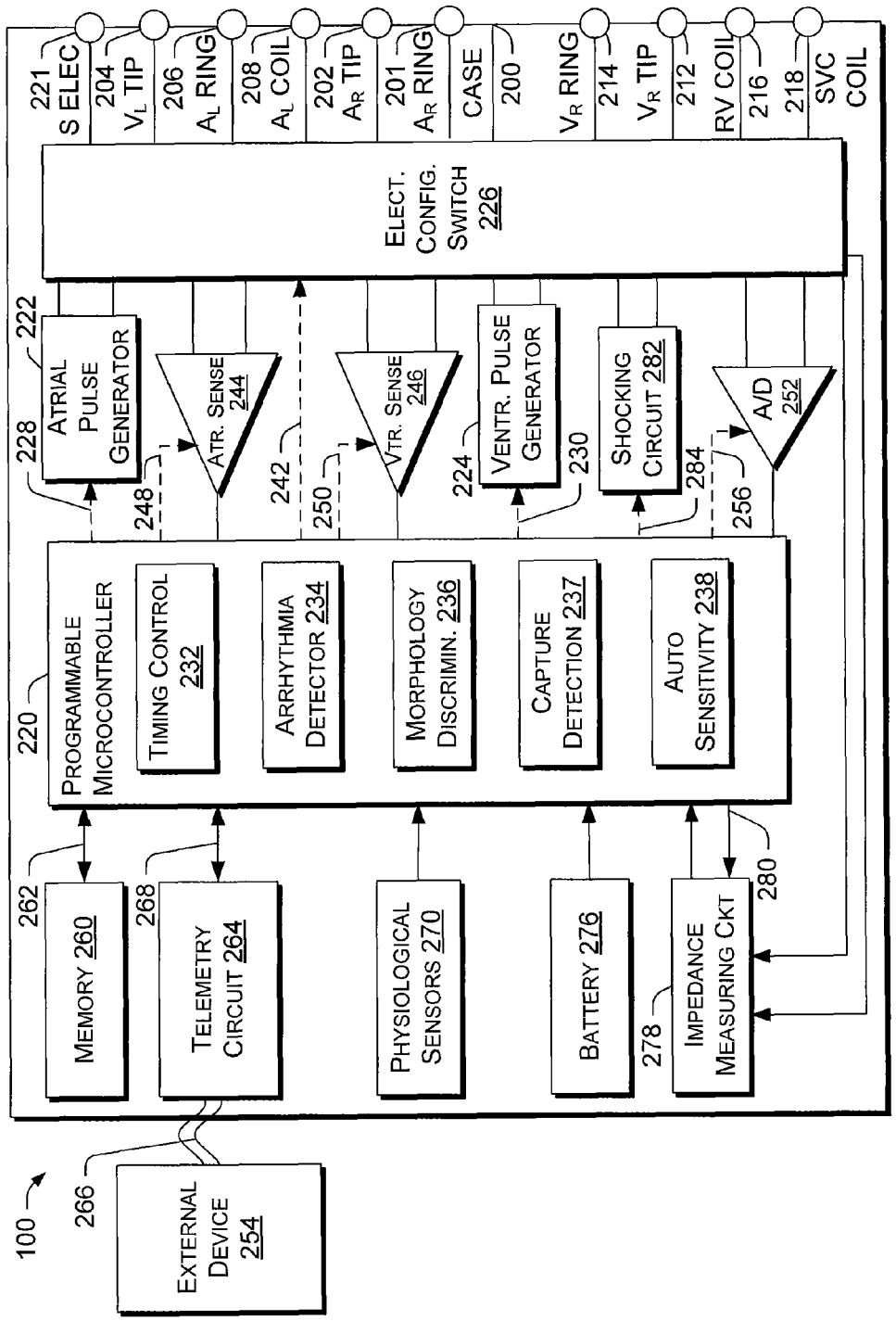
FIG. 2 is a functional block diagram of an exemplary implantable stimulation device illustrating basic elements that are configured to provide cardioversion, defibrillation, pacing stimulation and/or autonomic nerve stimulation or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, interatrial conduction (A-A) delay, or interventricular conduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234 and optionally an orthostatic compensator and a minute ventilation (MV) response module, the latter is not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes a morphology discrimination module 236, a capture detection module 237 and an auto sensing module 238. These modules are optionally used to implement various exemplary recognition algorithms and/or methods presented below. The aforementioned components may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention.

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (up to 0.5 J), moderate (0.5 J to 10 J), or high energy (11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Capture Detection Techniques

Referring again to the capture detection module 237 of the device 100 of FIG. 2, various techniques for capture detection may be used. In general, capture detection aims to verify capture following a delivered stimulus. For example, at a time $X_0$, a stimulus having amplitude $V_0$ is delivered per a ventricular pacing channel (see, e.g., the ventricular pulse generator 224 and associated circuitry). At approximately this time, a ventricular sensing channel (see, e.g., the sense circuit 246) initiates a blanking interval, B, during which no sensing occurs. Following the blanking interval, the ventricular sensing channel initiates an evoked response detection window, ERD, during which sensing of cardiac activity occurs. This activity is analyzed to decide whether an evoked response occurred; thus, verifying that the delivered stimulus resulted in successful capture. The decision process may be referred to generally as capture detection.

Often, capture detection is used to determine a suitable stimulus energy level, for example, one that results in capture while minimizing drain on a device's limited power supply. More generally, a capture detection algorithm is used in conjunction with a search technique that determine stimulation energy level may be referred to as threshold search algorithms in that they search for an appropriate stimulation threshold. Devices that implement threshold search algorithms may have difficulty distinguishing capture and non-capture for any of a variety of reasons. For example, fusion and/or pseudofusion waveforms may confound capture detection. Other examples are presented below.

Figure 3:
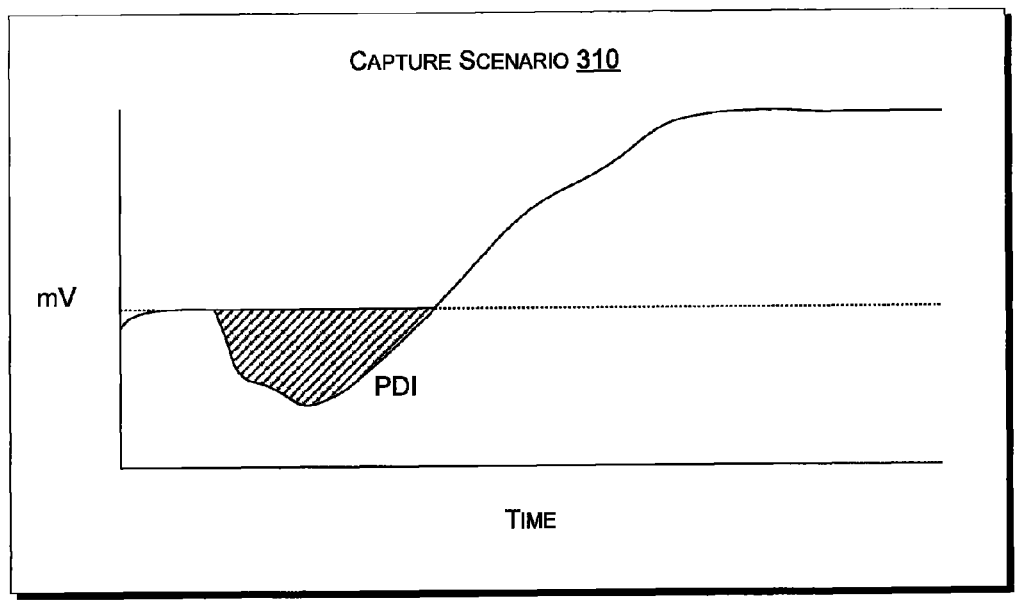
FIG. 3 is a cardiac electrogram plot of a capture scenario and a cardiac electrogram plot of a non-capture scenario where each plot indicates an approximate paced depolarization integral.
Figure 3:
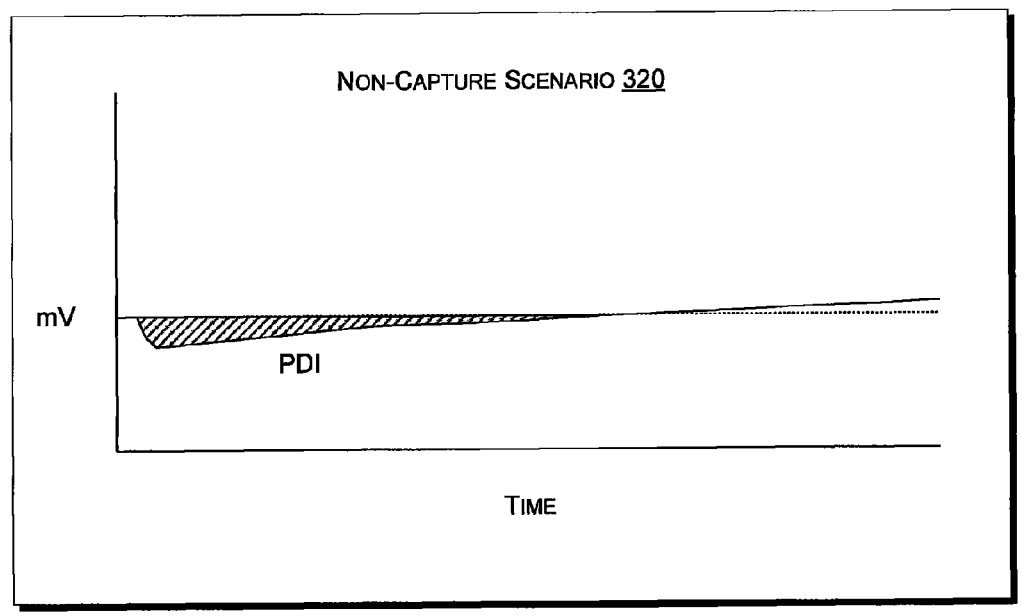

Regarding characteristics of capture and non-capture, FIG. 3 shows a cardiac electrogram for a capture scenario 310 and a cardiac electrogram for a non-capture scenario 320. Even though the signals are very different, the post-depolarization integral values, represented by the shaded areas, are similar. Of particular concern is the elevated PDI value for the non-capture cardiac electrogram 320.

Several factors contribute to elevated non-capturing PDI values. Sometimes the cardiac electrogram signal has not returned to its steady-state, baseline level before a pulse is delivered. This phenomenon can happen with large evoked response, large repolarization signals, far-field signals, and faster pacing rates. When a pacing pulse is delivered, various algorithms hold the cardiac electrogram signal amplitude constant during a software imposed recharge and block (e.g., Fast Recharge and Block Overlap) duration, which is typically on the order of several milliseconds. When this time expires, the cardiac electrogram signal returns to its intrinsic value, which after a non-capturing pulse on a low polarization lead, is now closer to its actual baseline level. The transition from a constant cardiac electrogram signal during block and recharge to an actual value looks like a small peak, and more importantly, has a significant PDI value.

Other techniques such as those that rely on an cardiac electrogram post-pulse slope (e.g., $D_{Max}$) can also experience difficulty in distinguishing capture and non-capture. Further, certain conventional techniques are limited to particular sensing configurations. For example, various PDI techniques are restricted to unipolar cardiac electrogram sensing (increased signal width) while various slope techniques are restricted to bipolar cardiac electrogram sensing (increased slope).

As described herein, various methods use morphology discrimination (sometimes abbreviated "MD") to distinguish capture and non-capture responsive to a pacing pulse. With morphology discrimination, peak(s), area(s), slope(s), shape(s), etc., of a waveform can be compared to a template to distinguish capture and non-capture. For example, while the two cardiac electrogram signals 310, 320 have similar PDI values, their peaks, slopes, and general shapes are very different. As explained below, morphology discrimination can be used to differentiate these two scenarios. Further, baselines differences from cardiac electrogram to cardiac electrogram can be easily addressed depending on the morphology used to perform a comparison. In some instances, baseline differences may not affect the comparison.

Conventional morphology discrimination typically relies on "dynamic template matching" to discriminate between normal and abnormal events such as atrial and ventricular tachyarrhythmias, which may be present in sensed cardiac activity (e.g., cardiac electrograms). Morphology discrimination enables a device to examine multiple characteristics of a cardiac electrogram, as opposed to techniques which may look only at a wave complex's width, integral, amplitude and/or slew rate (e.g., slope). As described herein, morphology discrimination allows for a comparison between a cardiac electrogram signal, or portion thereof, and a template. For example, morphology discrimination may compare a last acquired cardiac electrogram complex (e.g., QRS complex) with a predetermined physician-selected patient-specific template. Further, in such an example, the template may not necessarily "look" like a QRS complex but rather provide a standard for comparison.

In commercially available implementations of morphology discrimination, a MD algorithm is normally disabled in the setting of a delivered pacing pulse. In contrast, various exemplary methods described herein allow for morphology discrimination or other signal characterization following delivery of a pacing pulse (and optionally before and/or during delivery of an output pulse). In particular, various exemplary methods allow for capture detection even when a conventional evoked response sensing scheme may indicate otherwise (e.g., PDI, $D_{Max}$, etc.). More specifically, various exemplary methods allow a device to distinguish capture and non-capture scenarios (see, e.g., FIG. 3).

Some morphology discrimination techniques allow for automatic template update whereby a periodic evaluation of a stored template occurs followed by an update, which may be needed, for example, to accommodate changes in a patient's condition, a device's condition and/or a device/tissue interface. Various techniques allow for modification of a template and/or replacement of a template based on sensed cardiac activity (e.g., EGM information) or other information.

Various morphology discrimination techniques are described in U.S. Pat. No. 5,779,645, "System and method for waveform morphology comparison", to Olson et al., which is incorporated by reference herein. The '645 patent compares a test signal to a template signal to determine how closely the test and template signals correspond based on morphology. The comparison may use peak information in the template and the test signal and generate a score to indicate the degree of similarity between the template and the test signal.

Figure 4:
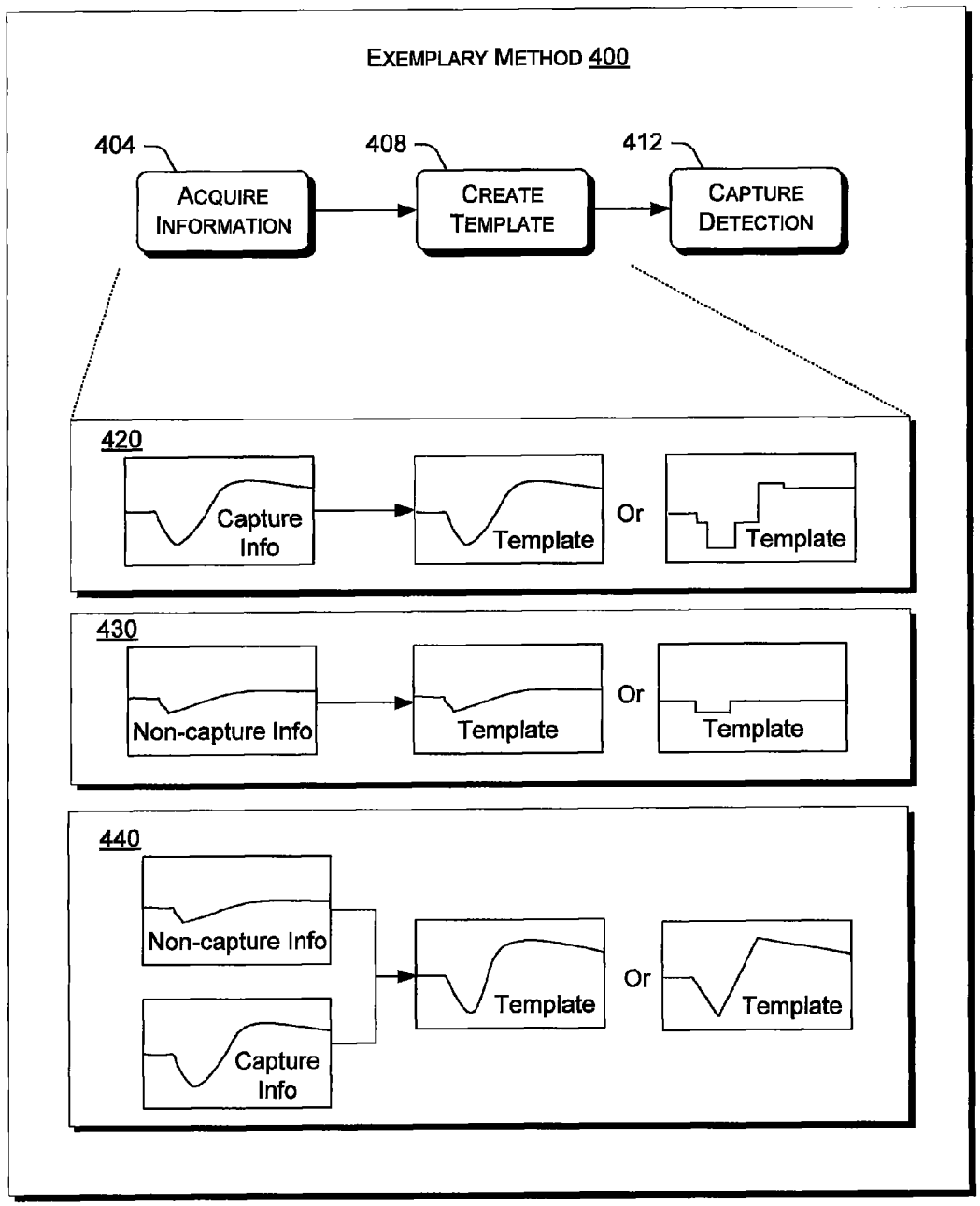
FIG. 4 is a block diagram of an exemplary method for creating a template and using the template for capture detection.

FIG. 4 shows an exemplary method 400 and associated variations. The method 400 acquires information in an acquisition block 404. A template creation or generation block 408 then uses this information to create a template. The method 400 then uses the template in a capture detection block 412.

Variations 420, 430 and 440 indicate how capture information may be used to create a template. In variation 420, cardiac electrogram information associated with capture is used to create a template. The template may be an unmodified representation of the EGM information or the template may be generated using a model that relies at least in part on the cardiac electrogram information. The variation 420 includes a template that is an exact or unmodified representation of the cardiac electrogram information as well as an alternative template. The capture detection block 412 may rely on one or more of such templates, i.e., a template based at least in part on capture information.

In variation 430, cardiac electrogram information associated with non-capture is used to create a template. The template may be an unmodified representation of the cardiac electrogram information or the template may be generated using a model that relies at least in part on the cardiac electrogram information. The variation 430 includes a template that is an exact or unmodified representation of the cardiac electrogram information as well as an alternative template. The capture detection block 412 may rely on one or more of such templates, i.e., a template based at least in part on non-capture information.

In variation 440, cardiac electrogram information associated with capture and EGM information associated with non-capture are used to create a template. The template may be generated using a model that relies at least in part on the capture and the non-capture cardiac electrogram information. The template of the variation 440 may have any shape that allows for distinguishing capture and non-capture. The capture detection block 412 may rely on one or more of such templates, i.e., a template based at least in part on capture information and at least in part on non-capture information.

As presented in the variations 420, 430, 440 of FIG. 4, a template may have a shape that allows for a comparison while not necessarily looking like the signal or signal portion to be compared to the template. For example, a template may look like a square wave, a series of square waves or a composite of square waves. In such an example, a certain error may be expected between the template and a signal where, if the error exceeds an error limit, a decision is made as to the nature of the signal or signal portion.

Various exemplary methods acquire cardiac electrogram information for use as a template, or creating a template, when pacing pulse energy is sufficiently high and likely to cause an evoked response. For example, an exemplary method may acquire information for a template during a threshold search and/or during an evoked response sensitivity test. Pacing devices typically perform threshold searches on a regular basis, for example, daily. A threshold search algorithm aims to select a pacing energy that balances a high likelihood of capture and power drain from a device's limited power supply.

A threshold search algorithm may occur in any of a variety of manners. Some algorithms perform top down searches (high energy to low energy) while others perform bottom up (low energy to high energy). Some algorithms call for delivery of a back-up pulse in instances where capture does not occur. A commercially available threshold search algorithm is known as the AUTOCAPTURE™ algorithm (St. Jude Medical Corp., Sylmar, Calif.).

Various exemplary threshold search methods may use a template to distinguish capture and non-capture. Such a template may be provided or based on cardiac electrogram information acquired during or immediately after a threshold search. Further, an exemplary method optionally acquires cardiac electrogram information for use as a non-capture template immediately before, during or immediately after a threshold search. As described herein, threshold searches may rely on morphology discrimination and/or other techniques to decide whether capture or non-capture occur following delivery of a pacing pulse.

An evoked response sensitivity test may be performed automatically on a predetermined basis or in response to an event or condition. In general, a clinician initiates an evoked response sensitivity test, for example, during an in-clinic consultation. An evoked response sensitivity test may be performed through use of a programmer configured to communicate with an implantable device (see, e.g., the computing device 730 of FIG. 7). For example, a programmer may include telemetry circuitry for wireless communication with an implanted device whereby an evoked response sensitivity test may be initiated. Such a programmer is typically capable of downloading cardiac electrograms and other information from an implantable device.

An evoked response sensitivity test may deliver a high-amplitude pacing pulse having a high certainty of capture. A cardiac electrogram acquired after delivery of the pulse may be stored and used as a template. A certain number of additional high-amplitude pulses may be delivered to confirm the template's accuracy. In addition, delivery of a low-amplitude pulse may be delivered (e.g., a 0 volt or 0.125 volt pulse) that has a high certainty of non-capture. The additional low-amplitude pulse may further confirm the template's accuracy and that its morphology is sufficiently different from the signal elicited after the capturing pulse. An exemplary method may optionally deliver a series of pacing pulses over a range of amplitudes followed by checking a template's accuracy.

Various exemplary methods may include use of one or more templates on a beat-to-beat basis for capture verification. Various exemplary methods may be implemented in conjunction with an implantable device configured to deliver cardiac resynchronization therapy, which may include bi-ventricular pacing therapy. Where more than one chamber of the heart is paced, a template may be suitable for use in capture determination for more than one chamber (e.g., a template suitable for use in left ventricular pacing and right ventricular pacing capture determinations). Where more than one chamber of the heart is paced, a template or group of templates may pertain to one chamber while another template or group of templates pertain to another chamber.

Figure 5:
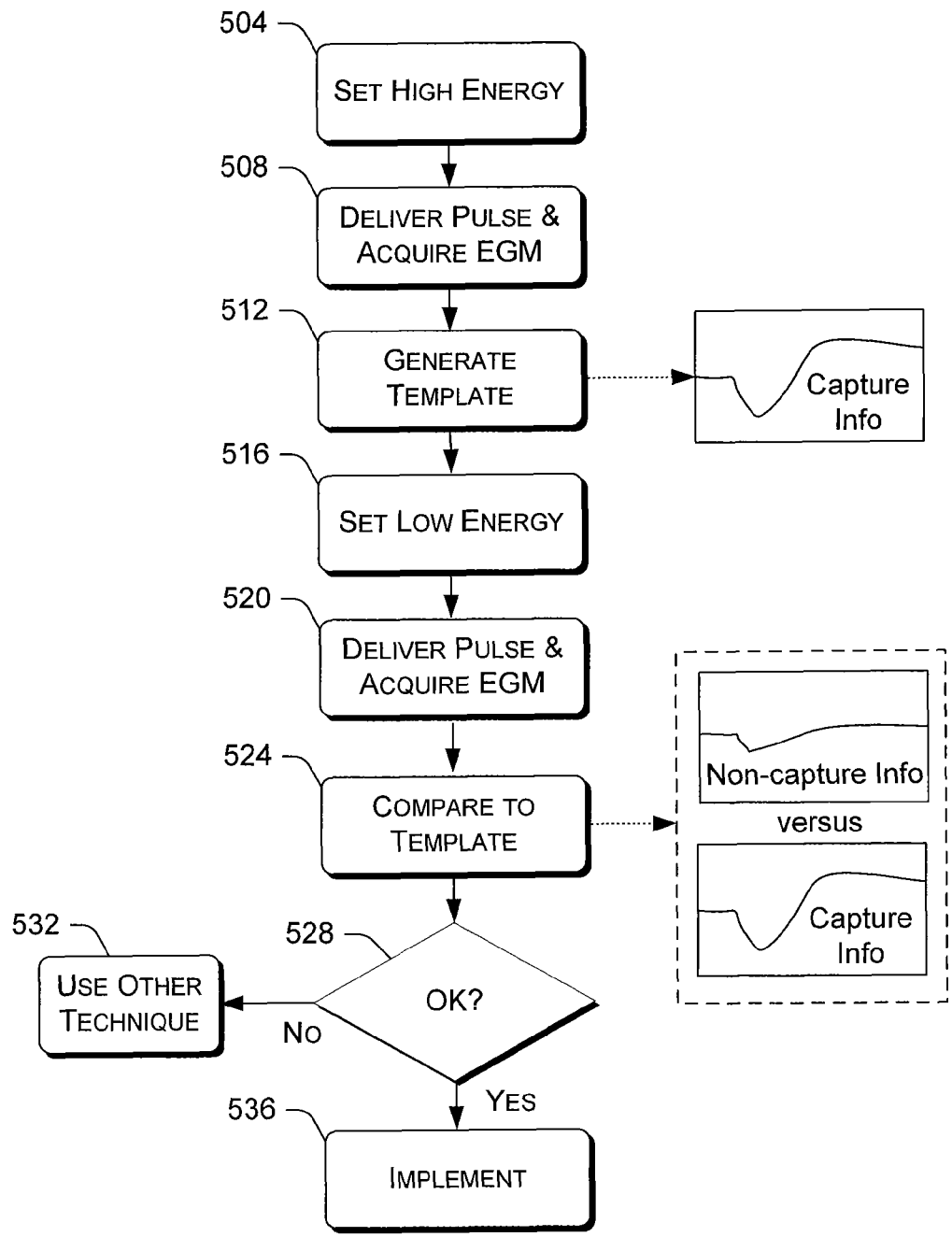
FIG. 5 is a block diagram of an exemplary method for assessing accuracy of a template or templates.

FIG. 5 shows an exemplary method 500 for acquiring information, generating a template and assessing the template's accuracy. The method 500 may be an evoked response sensitivity test such as a test normally used prior to implementation of an automatic capture assessment algorithm (e.g., the AUTOCAPTURE™ algorithm). The method 500 may include one or more actions germane to template acquisition, template generation, template comparison and/or template verification.

The method 500 commences in a set block 504 that sets pulse energy to a high level that is likely to cause capture (e.g., 4 V or higher). A delivery and acquisition block 508 follows that delivers a pulse using the high energy level and that acquires a cardiac electrogram (i.e., acquired information). A template generation block 512 generates a template based at least in part on the acquired cardiac electrogram. A raw cardiac electrogram may be used as a template or processing of a raw cardiac electrogram may occur. For example, more than one cardiac electrogram may be acquired and then averaged or one or more cardiac electrograms may be otherwise processed in an effort to allow for more accurate determinations of capture and/or non-capture.

Once the template has been generated, then the method 500 sets the energy to a low level or to zero per a set block 516. A delivery and acquisition block 520 follows that delivers the low energy or steps an implantable device through various steps that would typically occur for delivery of a pulse and acquire a cardiac electrogram pertaining to the delivery. A comparison block 524 follows that compares the acquired cardiac electrogram to the template for purposes of ensuring that the template can be used to distinguish capture and non-capture.

A decision block 528 optionally follows to decide if the comparison is robust or otherwise sufficient for use on an on-going basis. For example, an error or a confidence measure may be used to make such a decision. The decision may account for a particular therapy or patient condition. For example, if the patient is pacing dependent and the power supply of the pacing device at issue, then the decision block 528 may require a higher degree of certainty; whereas, for a non-pacing dependent patient and a device with adequate power, a lower degree of certainty may be required of the template's ability to distinguish capture and non-capture.

If the decision block 528 decides that the comparison is OK, then the method 500 implements the template per an implementation block 536. However, if the decision block 528 decides that the comparison is not OK, then another technique may be used for distinguishing capture and non-capture scenarios, per the block 532.

An exemplary method may optionally deliver pacing pulses at a range of amplitudes, checking the template for accuracy. Any of the various exemplary acquisition and/or accuracy check methods may execute automatically (e.g., outside of the clinic) on a periodic basis to ensure template accuracy.

While the method 500 includes some evoked response sensitivity test features, the method 500 may acquire a template outside the realm of an evoked response sensitivity test method and then use the template for one or more purposes that can benefit from capture and/or non-capture determinations.

As for specific examples where use of a template can be advantageous, consider a patient that requires fast pacing rates. In general, for fast pacing rates a cardiac electrogram signal has less time to return to baseline before the next pacing pulse, which can lead to elevated non-capturing PDI values. An exemplary method that uses a template for morphology discrimination would be able to tell that, while this sort of post-pace cardiac electrogram signal has a high area (PDI value), the waveform does not look like a normal captured waveform.

Morphology discrimination techniques described herein can also be implemented to overcome or more appropriately handle acute implants, injury current and other issues that can cause changes in capture/non-capture morphology. For example, newly implanted leads, injury current can lead to wider evoked responses and larger repolarization signals. These cardiac electrogram characteristics make it difficult for the cardiac electrogram signal to return to baseline before the next pacing pulse, again leading to higher non-capturing PDI values. An exemplary method that uses a template for morphology discrimination can differentiate capture and non-capture where such a return to baseline issue exists.

Injury current can also affect an evoked response waveform. In general, PDI techniques measure only "negative area" (i.e., area below a baseline value). An exemplary morphology discrimination method can compare any of a variety of waveform morphologies. For example, when injury current causes a shorter negative evoked response signal, which may or may not occur all within the block and recharge time, morphology discrimination can consider "positive" cardiac electrogram signals as well (i.e., above baseline characteristics). Additionally, with an automatically updating template algorithm, a threshold search algorithm (e.g., AUTOCAPTURE™) can be enabled at implant even if injury current is having a large effect on morphology. Even though injury current will subside and give rise to larger evoked responses, an AUTOCAPTURE™ algorithm can be enabled at implant with the automatically updating template algorithm.

An exemplary method that uses a template to distinguish capture and non-capture may be implemented using any of a variety of electrode configurations. For example, a convention PDI technique may require use of a particular electrode configuration for cardiac electrogram acquisition (e.g., unipolar or bipolar). Such requirements may further restrict the form of stored cardiac electrograms and interrogated real-time cardiac electrograms. An exemplary method that uses a template to distinguish capture and non-capture for purposes of threshold searches, or other operations, may use any of a variety of configurations. Further, an exemplary method may determine an optimal configuration or allow a clinician to select a desired configuration.

Figure 6:
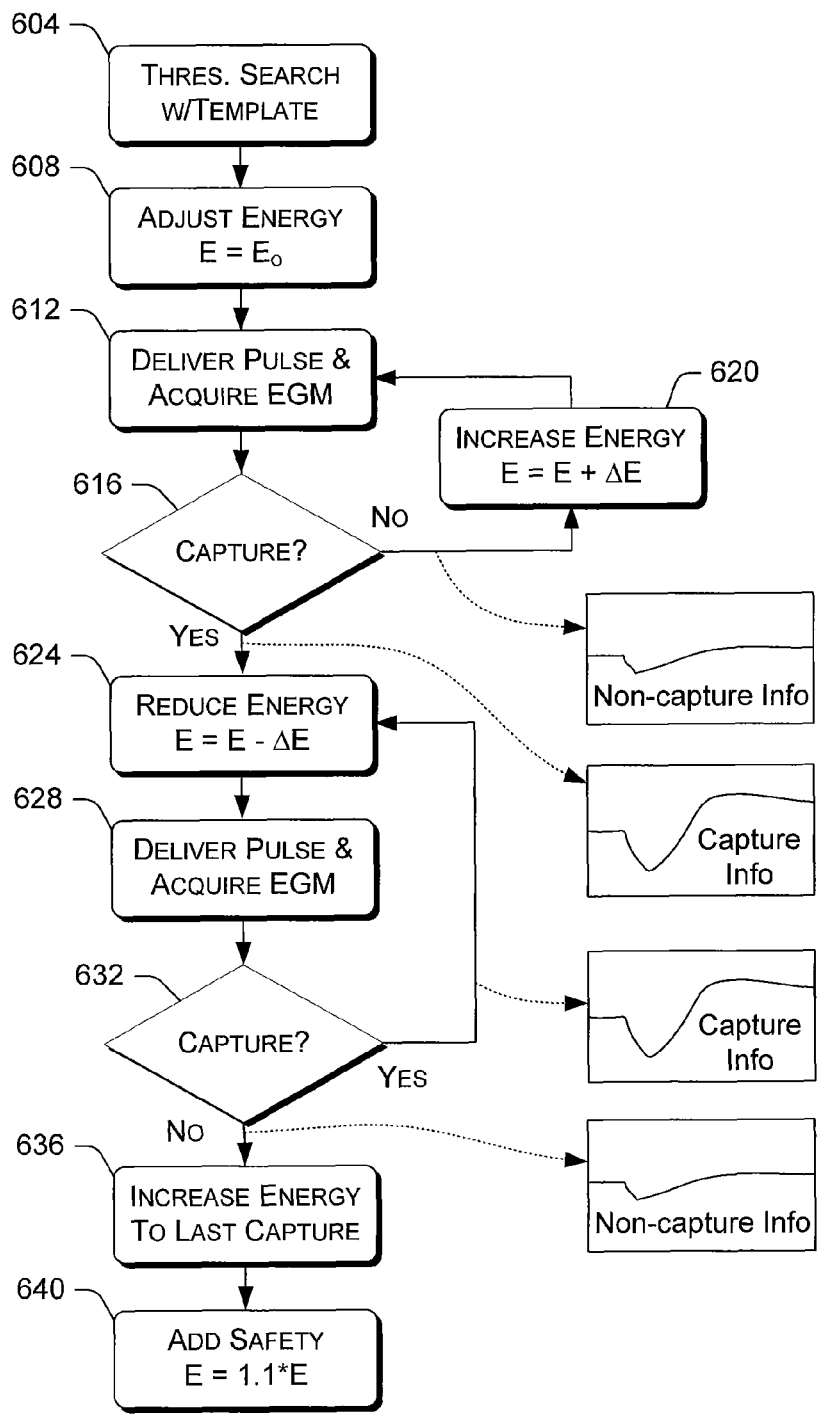
FIG. 6 is a block diagram of an exemplary method for acquiring cardiac electrogram information during a threshold search.

FIG. 6 shows an exemplary method for a threshold search 600 that includes use of one or more templates. Such a method may also acquire non-capture and/or capture information to confirm, generate or update a morphology discrimination template (see, e.g., templates 420, 430, and 440 of FIG. 4). The threshold search is initiated in block 604, which may occur after one or more non-capture determinations, at a scheduled time, upon a command issued by a care provider, etc. In this example, the threshold search uses one or more templates that may be stored in memory. One or more templates for other purposes may also be stored in memory (see, e.g., memory 260 of FIG. 2).

The method 600 then enters an adjustment block 608 that adjusts the pacing energy (e.g., $E=E_0$). Next, a delivery and acquisition block 612 calls for delivery of a pacing pulse and acquisition of a cardiac electrogram (e.g., an intracardiac electrogram). A decision block 616 decides if the pacing pulse caused an evoked response, i.e., capture. For example, the decision block 616 may make such a decision by comparing the cardiac electrogram to one or more templates. Typically, such a comparison uses a capture template (e.g., the template 420 of FIG. 4), however, a non-capture template (e.g., the template 430 of FIG. 4) may be used or a hybrid template (e.g., the template 440 of FIG. 4).

If the decision block 616 decides that capture did not occur, then the method 600 continues in an increase energy block 620 that increases the pulse energy (e.g., $E=E+\Delta E$). The method 600 then continues at the delivery block 612.

However, if the decision block 616 decides that capture occurred, then the method 600 enters an energy reduction block 624 that reduces the pulse energy (e.g., $E=E-\Delta E$). In this manner, the threshold search method 600 aims to ensure that pulse energy is not excessive (which may needlessly drain power). A delivery and acquisition block 628 delivers a pulse at the reduced energy and acquires a cardiac electrogram. Another decision block 632 follows that can make a decision as described for the decision block 616.

If the decision block 632 decides that capture occurred, then the method 600 continues at the reduction block 624 to further reduce the pulse energy. However, if the decision block 632 decides that capture did not occur, then the method enters a block 636 that increases the energy to the energy level that caused capture. Thereafter, an optional safety block 640 may further increase the energy level by a safety margin, which may be a percent, an energy amount, etc. Other action may be taken, as appropriate. Further, an adjustment for purposes of safety may occur elsewhere.

As indicated by various plots of capture information and non-capture information, the threshold search method 600 offers various opportunities to confirm, generate or update one or more templates based on capture and non-capture information in any of the acquired cardiac electrograms. For example, the decision block 616 and/or the decision block 632 may generate an error or a confidence measure based on a comparison of an acquired cardiac electrogram and a template or templates. If the error rises above a limit or the confidence measure falls below a limit, then information may be extracted from an acquired cardiac electrogram and used to update a template. Information acquired by blocks 612, 628 may be used to confirm, generate or update a template for use outside of a threshold search method or optionally for a subsequent threshold search (e.g., scheduled search or other search).

While an exemplary method may rely on a threshold search to acquire information for use in a template, other techniques also exist for acquisition of such information. An exemplary method may deliver a high-amplitude pacing pulse that is highly likely to cause capture. The method may then store the resulting cardiac electrogram waveform for use as a morphology discrimination template.

Such a method may use a certain number of additional high-amplitude pulses to confirm the template's accuracy. Alternatively, or in addition to, such a method may deliver zero energy (e.g., 0.0 V) or low energy (e.g., 0.125 V) pacing pulse that will not capture. In response, the method may confirm that the template is accurate enough to sufficiently distinguish the cardiac electrogram signal elicited after the non-capturing pulse. Further, timing adjustments may be made (e.g., to an atrial to ventricular interval) to avoid fusion. Yet further, a template may be shifted in time prior to or during a comparison to account for any timing adjustments.

Figure 7:
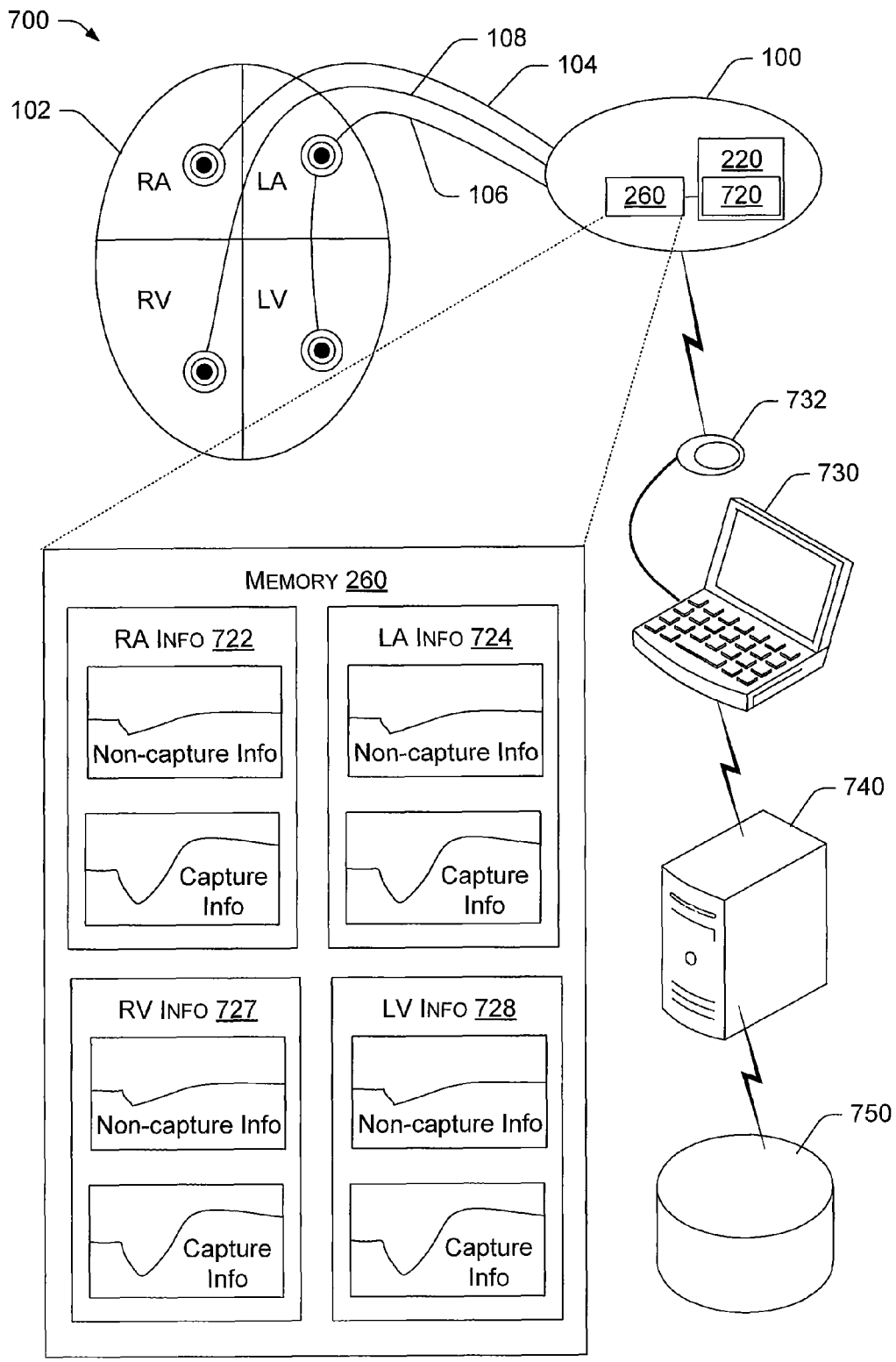
FIG. 7 is a diagram of exemplary components that acquire one or more templates and use the one or more templates for capture detection, observing trends, etc.

FIG. 7 shows an exemplary arrangement 700 for multi-chamber pacing. The device 100 includes memory 260 (see, e.g., FIG. 2) and leads 104, 106, 108 (see, e.g., FIG. 1) positionable to pace one or more chambers of the heart 102. For example, the device 100 may be configured to deliver cardiac resynchronization therapy in a manner that paces the right ventricle and the left ventricle. In such a scenario, capture and non-capture information may be acquired for each ventricle and where atrial pacing occurs, capture and non-capture information may be acquired for one or both atria.

Thus, the memory 260 of the device 100 may store capture and non-capture information for one or more chambers of the heart, as indicated by RA information 722, LA information 724, RV information 726 and LV information 728. Such information may be used by the device 100 for any of a variety of purposes.

As described herein, the device 100 optionally includes a module or control logic 720 that relies, at least in part, on one or more templates (e.g., capture templates) to optimize cardiac resynchronization therapy. For example, the module 720 may include instructions executable by the processor 220 (see, e.g., microcontroller 220 of FIG. 2) to optimize cardiac resynchronization therapy based on a right ventricular template (e.g., RV information 726) and a left ventricular template (e.g., LV information 728). In particular, the module 720 may compare a right ventricular template to a left ventricular template to uncover changes in capture morphology over time. More specifically, a shape factor that depends on one or more post-pulse cardiac electrogram peaks (e.g., peak timing, peak amplitude, etc.) may be used to determine relative changes in ventricular evoked responses. Such changes may then be used automatically or through a clinician to adjust or otherwise optimize one or more cardiac resynchronization parameters.

While the device 100 may have such capabilities per the module 720, such capabilities may be available alternatively or additionally in a computing device 730 (e.g., a programmer for an implantable device) capable of communicating with the device 100 (e.g., wand or paddle 732) and/or another computer 740. Further, the information 722-728 may be communicated to a database 750. Aggregation or results of a statistical analysis of information from a variety of patients may be used in determining an appropriate course of therapy. For example, the database 750 may include data from other patients and the computer 740 (or other computer) may include a model that relies on the data from other patients and a particular patient to recommend a course of action for the particular patient.

An exemplary method may include providing a template, delivering a right ventricular pacing pulse to a heart and a left ventricular pacing pulse to the heart, acquiring a cardiac electrogram, comparing the cardiac electrogram to the template and, based on the comparing, deciding if the right ventricular pacing pulse caused an evoked response and/or if the left ventricular pacing pulse caused an evoked response. In this example, the template may be based on a cardiac electrogram that includes information for a right ventricular evoked response and a left ventricular evoked response. Such a template may be acquired using a high energy level for right and left ventricular pacing pulses and such a template may be optionally assessed for accuracy, as described above, using appropriate modifications to account for bi-ventricular pacing. For example, the template may account for a delay between delivery of right and left ventricular pulses, be partitionable into right and left ventricular portions, assessed for left ventricular accuracy (e.g., using a left ventricular portion of the template), assessed for right ventricular accuracy (e.g., using a right ventricular portion of the template), etc.

A template may rely on superposition of a cardiac electrogram for a right ventricle and a cardiac electrogram for a left ventricle. Superposition states that the total response at a given place and time caused by two or more signals propagating in the same space is the sum of the separate responses which would have been produced by the individual signals. Where left ventricular and right ventricular pacing occur, a template based on superposition of a left ventricular template and right ventricular template may be used, optionally accounting for a delay between delivery of right and left ventricular pulses if the pulses are not delivered simultaneously.

An exemplary method includes providing a template, delivering a right ventricular pacing pulse to a heart and a left ventricular pacing pulse to the heart, acquiring a cardiac electrogram, comparing the cardiac electrogram to the template and, based on the comparing, deciding if the right ventricular pacing pulse caused an evoked response and/or if the left ventricular pacing pulse caused an evoked response where the template is a superposition of a cardiac electrogram for a left ventricular evoked response and a cardiac electrogram for a right ventricular evoked response where the superposition optionally relies on a delay between delivery of the right ventricular pacing pulse and the left ventricular pacing pulse.

Various exemplary methods may store template information, comparison results, etc., for the purposes of trend analysis. For example, a series of templates spanning several months may be analyzed to reveal a trend. Such a trend may relate to characteristics of a device (e.g., condition of device), one or more tissue/device interfaces, patient condition, etc.

While various examples refer to pacing pulse voltages such as those used in constant voltage pacing, other pacing methods may use constant current or other energy parameters for pacing. As described herein, morphology discrimination can be used for any of these pacing techniques to distinguish capture and non-capture. Again, morphology discrimination can alleviate restrictions as to electrode sensing configurations as well. Such flexibility can be advantageous in instances where a device can select or alter pacing or sensing configurations to improve cardiac performance. In other words, a conventional capture assessment technique may limit such options.

Conclusion

Although exemplary methods and/or devices have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods and/or devices.

The invention claimed is:

1. In an implantable medical device, a method comprising:
providing a template;
delivering a pacing pulse to a heart;
acquiring a cardiac electrogram;
comparing the cardiac electrogram to the template;
based on the comparing, deciding if the pacing pulse caused an evoked response; and
assessing accuracy of the template by delivering a pulse at an energy level unlikely to cause an evoked response, acquiring a second cardiac electrogram and using the second cardiac electrogram to assess accuracy of the template, and automatically switching, within the implantable medical device, to a different evoked response determination if the accuracy of the template is not sufficient.

2. The method of claim 1 wherein the providing a template comprises performing an evoked response sensitivity test.

3. The method of claim 1 wherein the providing comprises assessing accuracy of the template by delivering a pulse at an energy level likely to cause an evoked response, acquiring a cardiac electrogram and using the cardiac electrogram to assess accuracy of the template.

4. The method of claim 1 wherein the comparing compares morphology of the cardiac electrogram to morphology of the template.

5. The method of claim 1 wherein the method occurs during a threshold search.

6. The method of claim 1 wherein the template comprises a template updated using a cardiac electrogram acquired during a threshold search.

7. The method of claim 1 wherein, if the deciding decides that the pacing pulse caused an evoked response, further comprising updating the template based at least in part on the cardiac electrogram.

8. The method of claim 1 further comprising assessing accuracy of the template by selecting a maximum pacing pulse energy level, delivering a pacing pulse using the maximum pacing pulse energy level, acquiring a cardiac electrogram for the pacing pulse and using the cardiac electrogram to assess accuracy of the template.

9. The method of claim 1 wherein the delivering delivers the pacing pulse to the right ventricle of the heart and wherein the template comprises a right ventricular capture template.

10. The method of claim 1 wherein the delivering delivers the pacing pulse to the left ventricle of the heart and wherein the template comprises a left ventricular capture template.

11. The method of claim 1 wherein the delivering delivers the pacing pulse to an atrium of the heart and wherein the template comprises an atrial capture template.

* * * * *